US005656613A

United States Patent [19]
Bull et al.

[11] Patent Number: 5,656,613
[45] Date of Patent: Aug. 12, 1997

[54] TREATMENT OF HYPERANDROGENIC CONDITIONS

[75] Inventors: Herb G. Bull, Westfield; Georgianna S. Harris, Tinton Falls, both of N.J.

[73] Assignee: Merck & Co., Inc., Rahway, N.J.

[21] Appl. No.: 368,513

[22] Filed: Jan. 4, 1995

[51] Int. Cl.$^6$ .................................................. A61K 31/70
[52] U.S. Cl. ....................... 514/47; 514/46; 514/169; 514/172; 514/176; 514/177; 514/253; 536/26.24; 544/77; 544/78
[58] Field of Search .................. 514/284, 47, 46, 514/177, 253, 169, 172, 176; 546/77, 78; 536/26.24; 544/77, 78

[56] References Cited

U.S. PATENT DOCUMENTS

| | | | |
|---|---|---|---|
| 4,220,775 | 9/1980 | Rasmusson et al. | 546/77 |
| 4,377,584 | 3/1983 | Rasmusson et al. | 514/284 |
| 4,760,071 | 7/1988 | Rasmusson et al. | 514/284 |
| 4,845,104 | 7/1989 | Carlin et al. | 514/284 |
| 5,021,571 | 6/1991 | Mease et al. | 544/166 |
| 5,049,562 | 9/1991 | Rasmusson et al. | 514/284 |
| 5,061,801 | 10/1991 | Williams et al. | 546/77 |
| 5,061,802 | 10/1991 | Steinberg et al. | 546/77 |
| 5,061,803 | 10/1991 | Williams | 546/77 |
| 5,075,450 | 12/1991 | Rasmusson et al. | 546/285 |
| 5,084,574 | 1/1992 | Bhattacharya et al. | 546/77 |
| 5,091,380 | 2/1992 | Rasmusson et al. | 514/169 |
| 5,091,534 | 2/1992 | King et al. | 546/14 |
| 5,098,908 | 3/1992 | Steinberg et al. | 514/284 |
| 5,120,742 | 6/1992 | Rasmusson et al. | 514/284 |
| 5,138,063 | 8/1992 | Rasmusson et al. | 546/77 |
| 5,151,429 | 9/1992 | Rasmusson et al. | 514/284 |
| 5,151,430 | 9/1992 | Steinberg et al. | 514/284 |
| 5,162,322 | 11/1992 | Taylor, Jr. et al. | 514/252 |
| 5,196,411 | 3/1993 | Rasmusson et al. | 514/169 |
| 5,215,894 | 6/1993 | Arison et al. | 435/53 |
| 5,237,061 | 8/1993 | Bhattacharya et al. | 544/125 |
| 5,237,064 | 8/1993 | Bakshi et al. | 546/14 |
| 5,237,067 | 8/1993 | Schumaker | 546/187 |
| 5,278,159 | 1/1994 | Bakshi et al. | 546/77 |
| 5,324,734 | 6/1994 | Gilbert et al. | 514/284 |
| 5,422,262 | 6/1995 | Andersson et al. | 546/77 |
| 5,510,351 | 4/1996 | Graham et al. | 514/253 |
| 5,510,485 | 4/1996 | Graham et al. | 546/77 |
| 5,543,417 | 8/1996 | Waldstreicher | 514/253 |
| 5,583,138 | 12/1996 | Tuba et al. | 546/77 |

FOREIGN PATENT DOCUMENTS

| | | |
|---|---|---|
| 0 285 382 A2 | 5/1988 | European Pat. Off. |
| 0 285 383 A2 | 5/1988 | European Pat. Off. |
| 93/23040 | 11/1993 | WIPO |
| 93/23041 | 11/1993 | WIPO |
| 93/23048 | 11/1993 | WIPO |
| 93/23050 | 11/1993 | WIPO |
| 93/23051 | 11/1993 | WIPO |
| 93/23419 | 11/1993 | WIPO |
| 93/23420 | 11/1993 | WIPO |
| 94/07861 | 4/1994 | WIPO |
| 94/20104 | 9/1994 | WIPO |

OTHER PUBLICATIONS

The Daily (Tuesday, May 7, 1996), "New Data on Proscar, Abbott's Hytrin Show Conflicting Results".
Wall Street Journal (Tuesday, May 7, 1996), "Study Finds Abbott's Prostate Drug is Much More Effective than Merck's", p. B4.
US News & World Report, May 20, 1996, "Zapping a problem prostate".
Rasmusson et al., J. Med. Chem., Azasteroids: Structure–Activity Relationships for Inhibition of 5–alpha–Reductase and of Androgen Receptor Binding, (1986), 29, 2298–2315.
Everse et al., Bioorganic Chemistry, Addition Products of Diphosphopyridine Nucleotides with Substrates of Pyridine Nucleotide–Linked Dehydrogenases, (1971) 1, 207–233.
Tian et al., Biochemistry, 17–beta–(N–tert–Butylcarbamoyl)–4– aza–5alpha–androstan–1–en–3–one Is an Active Site–Directed Slow Time–Dependent Inhibitor of Human Steroid 5–alpha–Reductase 1, (1994), 33, 2291–2296.
Faller et al., Biochemistry, Finasteride: A Slow–Binding 5–alpha–Reductase Inhibitor, (1993) 32, 5705–5710.
Harris et al., Proc. Natl. Acad Sci., Identification and selective inhibition of an isozyme of steriod 5–alpha–reductase in human scalp, (1992), 89, 10787–10791.
Gormley et al., Journal of Clinical Endocrinology and Metabolism, Effects of Finasteride (MK–906), a 5–alpha–Reductase Inhibitor, on Circulating Androgens in Male Volunteers*, (1990), 70:4, 1136–1141.
Elizabeth Stoner, J. Steroid Biochem., Molec. Biol., The Clinical Development of a 5–alpha–Reductase Inhibitor, Finasteride, (1990), 37:3, 375–378.
Neri et al., Endo, A Biological Profile of a Nonsteroidal Antiandrogen, SCH 13521 (4'–Nitro–3'–Trifluoromethylisobutyranilide), (1972) 91:2, 427–437.

*Primary Examiner*—James O. Wilson
*Attorney, Agent, or Firm*—Catherine D. Fitch; Melvin Winokur

[57] ABSTRACT

The invention concerns the treatment of hyperandrogenic conditions in humans by the formation of a novel mechanism-based irreversible inhibitor of human 5α-reductase enzymes from 3-oxo-4-azasteroids having a 1,2-double bond and the pyridine-nucleotide cofactor of the 5α-reductase enzyme, NADPH. Until the present invention, it was not known or predicted that 3-oxo-4-azasteroids having a 1,2-double bond would form a complex with NADPH by the mechanism of 5α-reductase in vivo. The invention further relates to the novel inhibitor-cofactor complex and pharmaceutical compositions containing the complex.

8 Claims, No Drawings

TREATMENT OF HYPERANDROGENIC CONDITIONS

SUMMARY OF THE INVENTION

The invention concerns the treatment of hyperandrogenic conditions in humans by the formation of a novel mechanism-based irreversible inhibitor of human 5α-reductase enzymes from 3-oxo-4-azasteroids having a 1,2-double bond and the pyridine-nucleotide cofactor of the 5α-reductase enzyme, NADPH. The invention further relates to the isolated inhibitor-cofactor complex.

BACKGROUND OF THE INVENTION

Certain undesirable physiological manifestations, such as acne vulgaris, seborrhea, female hirsutism, androgenic alopecia which includes female and male pattern baldness, and benign pro static hyperplasia, are the result of hyperandrogenic stimulation caused by excessive accumulation of testosterone ("T") or similar androgenic hormones in the metabolic system. Androgenic alopecia is also known as androgenetic alopecia. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethyl-isobutyranilide. See Neri, et al., Endocrinol. 1972, 91 (2). However, these products, though devoid of hormonal effects, compete with all natural androgens for receptor sites, and hence have a tendency to feminize a male host or the male fetus of a female host and/or initiate feed-back effects which would cause hyperstimulation of the testes.

The principal mediator of androgenic activity in some target organs, e.g. the prostate, is 5α-dihydrotestosterone ("DHT"), formed locally in the target organ by the action of testosterone-5α-reductase. Inhibitors of testosterone-5α-reductase will serve to prevent or lessen symptoms of hyperandrogenic stimulation in these organs.

The enzyme 5α-reductase catalyzes the reduction of testosterone to the more potent androgen, dihydrotestosterone, as shown below:

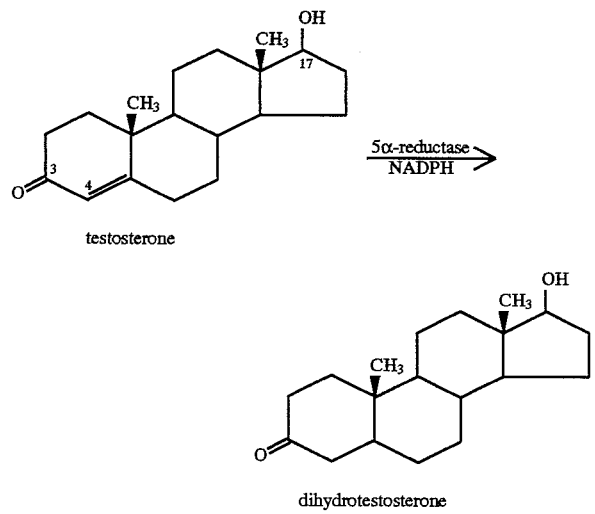

Finasteride, (17β-(N-tert-butylcarbamoyl)-3-oxo-4-aza-5α-androst-1-ene-3-one) as shown below, is a potent inhibitor of the human prostate enzyme.

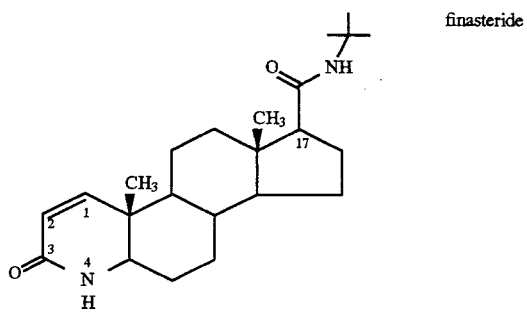

Under the trade name PROSCAR®, finasteride is known to be useful in the treatment of hyperandrogenic conditions; see eg. U.S. Pat. No. 4,760,071. Finasteride is currently prescribed for the treatment of benign prostatic hyperplasia (BPH), a condition afflicting to some degree the majority of men over age 55. Finasteride's utility in the treatment of androgenic alopecia and prostatic carcinoma is also disclosed in the following documents: EP 0 285,382, published 5 Oct. 1988; EP 0 285,383, published 5 Oct. 1988; Canadian Patent no. 1,302,277; and Canadian Patent no. 1,302,276.

There are two isozymes of 5α-reductase in humans. One isozyme (type 1) predominates in sebacious glands of facial and skin tissue and is relatively insensitive to finasteride; the other (type 2) predominates in the prostate and is potently inhibited by finasteride.

In clinical trials, the efficacy of finasteride far exceeded expectations based on its perceived potency against the human prostate enzyme, for which finasteride was first thought to be a simple, rapidly-reversible inhibitor with $K_i$=26 nM. For instance, circulating concentrations of finasteride comparable to this Ki actually reduced levels of dihydrotestosterone to values approaching those found in individuals genetically deficient in the prostate isozyme, and as long as two weeks were required for dihydrotestosterone to return to basal levels after withdrawal of finasteride (Stoner, J. Steroid. Biochem. Molec. Biol. 37:375–378 (1990) and Gormley et al., J. Clin. Endocrinol. Metabol. 70:1136–1141 (1990)). A closer evaluation of the interaction of finasteride with the human prostate (type 2) isozyme led to appreciation that finasteride and certain analogs thereof are slow-binding inhibitors, such that their potency had been mistakenly underrated in standard fixed-time assays (Harris et al., Proc. Natl. Acad. Sci. U.S.A., 89:10787–10791 (1992)). Independently, Faller et al., also recognized the inconsistency. Faller et al., have recently described in detail the slow-binding behavior of finasteride, reaching the conclusion that finasteride binds to the human prostate isozyme with a rate constant of $2.7 \times 10^5$ $M^{-1}s^{-1}$ to form an essentially irreversible enzyme-inhibitor complex with a $K_i$<<1 nM (Faller et al., Biochemistry 32:5705–5710 (1993)).

Although finasteride is not a significant inhibitor of human skin (type 1) isozyme at doses employed in the treatment of BPH, finasteride does slowly form a comparable high affinity complex with this isozyme. As determined by Tian, et al., Biochemistry 33:2291–2296 (1994), the second-order rate constant for formation of this complex is $4.0 \times 10^3$ $M^{-1}s^{-1}$, which is about 1% of the rate constant against the prostate isozyme. Based on the apparent irreversible inhibition and on structure-activity considerations, Tian et al., proposed that finasteride binds to the enzyme covalently as a Michael acceptor.

The present invention demonstrates, in contrast to the expectation in the art, that finasteride and other 3-oxo-4- azasteroids having a 1,2 double bond are novel mechanism-based irreversible inhibitors of 5α-reductase. These 3-oxo-4-azasteroids having a 1,2-double bond are recognized as a substrate by the human 5α-reductase type 1 and type 2 enzymes, and in the course of the enzymatic reduction, the 3-oxo-4-azasteroid having a 1,2-double bond forms a covalent adduct with the pyridine-nucleotide cofactor (NADPH). The inhibitor-cofactor complex formed between dihydrofinasteride cation and the oxidized nicotinamide cofactor is bound by the enzyme as a potent collected-product inhibitor with a $K_i < 3 \times 10^{-13} M$.

Kaplan et al. (Everse et al., Bioorganic Chem. 1:207–233 (1971)) in their work with pyridine nucleotide-linked dehydrogenases identified analogous high-affinity, abortive ternary complexes formed spontaneously (in the reverse direction) by several pyridine nucleotide-linked dehydrogenases, notably lactate dehydrogenase. Lactate dehydrogenase mistakenly adds pyruvate to NAD+ to form the inhibitor shown below:

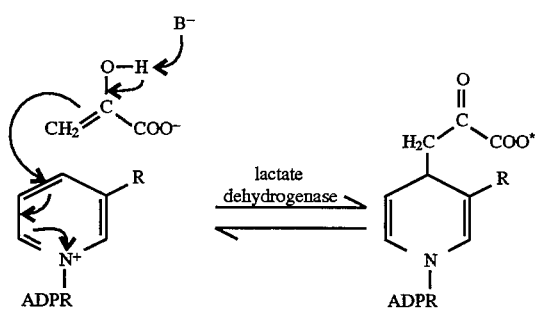

wherein B⁻ represents a basic group on the enzyme active site and ADPR represents adenosine-diphospho-ribose.

Processes for inserting the 1,2 double bond in a steroid analog are described in U.S. Pat. Nos. 5,084,574 and 5,021,571. Preparation of 3-oxo-4-azasteroids having a 1,2 double bond is described in the following publication: Rasmusson et al., J. Med. Chem. 29:2298–2315 (1986).

DETAILED DESCRIPTION OF THE INVENTION

Novel mechanism-based irreversible inhibitors of human 5α-reductase enzymes are formed from 3-oxo-4-azasteroids having a 1,2-double bond and the pyridine-nucleotide cofactor of the 5α-reductase enzyme NADPH. The structure of the covalent NADP-inhibitor complex, which has been isolated in substantially pure form, is represented below as structural formula (I):

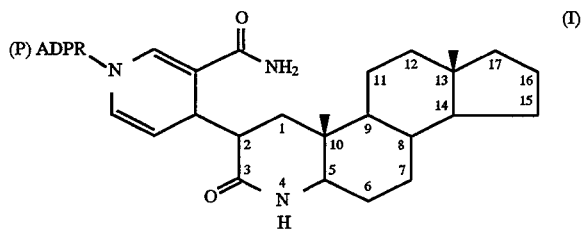

wherein (P)ADPR signifies 2-phospho-adenosine-diphospho-ribose.

The covalent adduct of structural formula (I) may optionally be modified as known to those in the art so long as there was no substitution at the 4-nitrogen and the 3-oxo position was conserved. Particularly preferred are compounds substituted at any of the following positions of the azasteroid ring: 7,15,16 and 17, depending on the structure of the 3-oxo-4-azasteroid having a 1,2-double bond administered to the human being.

The mechanism for inhibition of the 5α-reductase enzyme is proposed in Scheme 1. There is a close parallel between reduction of the natural substrate, testosterone, and reduction of 3-oxo-4-azasteroid inhibitors having a 1,2-double bond, since both proceed through nearly identical high-energy enolates. In the case of testosterone, transfer of hydride ion to C-5 gives the 3,4-enolate, and the reduction is completed by transfer of a proton to C-4 to allow tautomerization to dihydrotestosterone. In the case of 3-oxo-4-azasteroid inhibitors having 1,2-double bond, transfer of hydride ion to C-1 gives the 2,3-enolate instead. It is certain that this hydride transfer is essentially complete in the high-affinity complex, since no untransformed 3-oxo-4-azasteroid inhibitor having a 1,2-double bond is recovered upon denaturation of the enzyme-inhibitor complex. At this point the enzyme becomes trapped, being unprepared to transfer a proton to C-2 to complete the reduction. Unable to find a proton, the enolate/carbanion attacks the positively charged pyridinium ion to produce the covalent adduct, which the enzyme binds tenaciously.

The enzyme-inhibitor complex decomposes spontaneously with a halflife of about 1 month, and the dihydro-3-oxo-4-azasteroid inhibitor is the only product recovered.

Scheme 1c:

testosterone

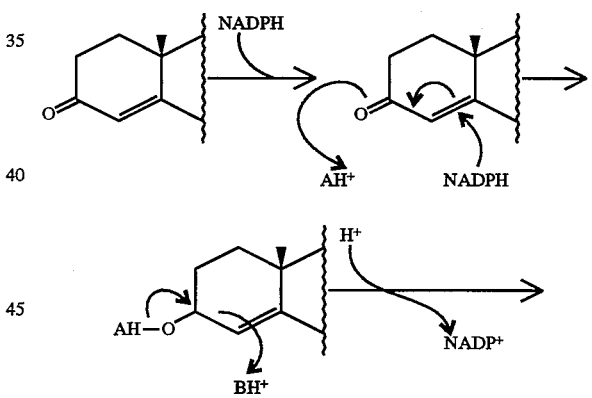

dihydrotestosterone 3-oxo-4-aza inhibitor with 1,2-double bond

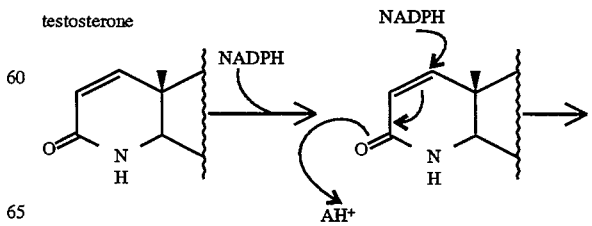

Scheme 1c:

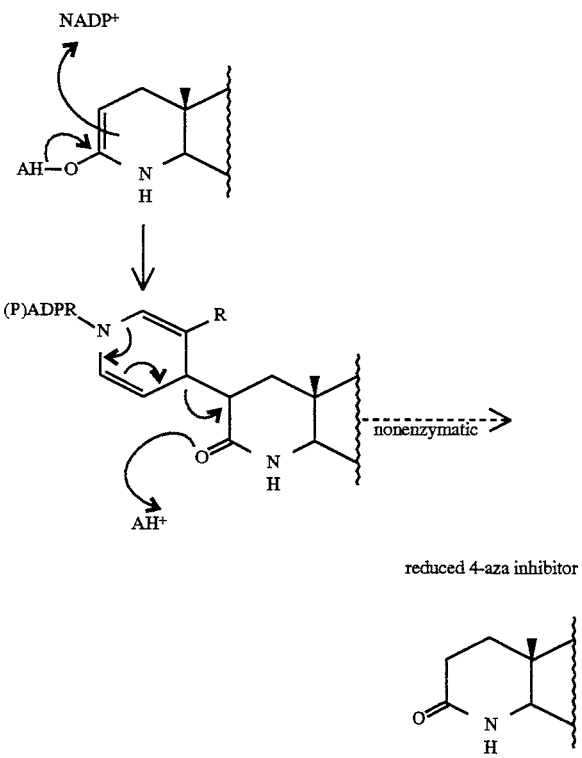

reduced 4-aza inhibitor wherein AH and BH represent proton donors in the enzyme active site and (P)ADPR represents 2-phospho-adenosine-diphospho-ribose.

3-oxo-4-azasteroids having a 1,2-double bond (also called $\Delta^1$NH-azasteroids) are selectively activated by the enzyme 5α-reductase to produce the novel covalent adduct with the cofactor NADPH of structural formula (I).

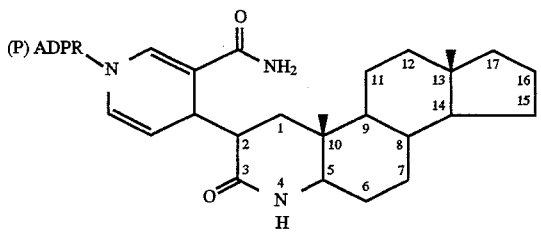

Especially preferred 3-oxo4-azasteroids having a 1,2-double bond useful in the present invention are the compounds of structural formula II, below:

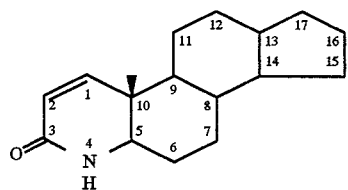

Processes for inserting the 1,2-double bond in a 3-oxo-4-azasteroid are described in U.S. Pat. Nos. 5,084,574 and 5,021,571. The azasteroid of structural formula II may optionally be substituted. In particular, the azasteroid of structural formula II may optionally be substituted in position-17 with an ether or thioether as described in PCT publication WO 93/23040; or an anilide as described, for example, in PCT publication WO 94/07861, or unsubstituted, monosubstituted or disubstituted amides as described in PCT publications WO 93/23038, WO 93/23051, WO 93/23420, and U.S. Pat. Nos. 4,220,775; 4,760,071; 4,845,104; 5,237,067; 5,091,380; 5,061,801; 5,215,894, or oxo as described in U.S. Pat. Nos. 4,220,775; 4,377,584 or hydroxy as described in U.S. Pat. Nos. 4,220, 775; 4,377,584 or cyano as described in U.S. Pat. No. 4,220,775 or tetrazolyl as described in U.S. Pat. No. 4,220, 775 or arylalkylcarbonyloxy alkyl as described in U.S. Pat. No. 4,377,584 or cycloalkylarylcarbonyloxy alkyl as described in U.S. Pat. No. 4,377,584 or benzoyloxyalkyl as described in U.S. Pat. No. 4,377,584 or acyl, substituted or unsubstituted, as described in U.S. Pat. Nos. 5,049,562; 5,138,063; 5,151,429; 5,237,061; 5,120,742; 5,162,332; 5,061,802; 5,098,908; 5,196,411; 5,075,450; 5,061,803; 5,324,734 or thiobenzoyl as described in U.S. Pat. No. 5,151,430 or polyaroyl as described in U.S. Pat. No. 5,162, 322 or ester as described in U.S. Pat. No. 5,091,534, and PCT Publications WO 93/23041, WO 93/23040 or alkyl, either substituted or unsubstituted, as described in PCT publications WO 93/23050, WO 93/23419, WO 93/23051 or urea, thiourea, carbamate or thiocarbamate as described in PCT publications WO 93/23048, or thioester as described in PCT publications WO 93/23041, WO 93/23040.

The azasteroid of structural formula II may further be optionally substituted at position-16 with: lower alkyl as described in PCT publication 93/23039, and U.S. Pat. Nos. 5,049,562; 5,138,063; 5,278,159; and 4,377,584 or hydroxyl as described in U.S. Pat. Nos. 5,278,159 and 4,377,584.

The azasteroids of structural formula II may optionally be further substituted at position-15 with alkyloxy, alkyl or cyano as described in PCT publication WO 94/20104.

The azasteroid of structural formula II may further be substituted at position-7 as with a loweralkyl group as described in U.S. Pat. No. 4,220,775. The formation of a 7-β bond is described in U.S. Pat. No. 5,237,064.

Additional substitutions on the azasteroid as known in the art are permissible, with the exception of the A ring, which may not contain additional substitution.

In order to enhance binding with the 5α-reductase type 2 enzyme it is preferable that position-17 be substituted with a hydrophobic group. Especially preferred are compounds having amide or anilide substitution at position-17.

Azasteroids selective for the 5α-reductase type 1 enzyme are described in PCT publication WO 93/23420.

Azasteroids selective for both 5α-reductase type 1 and type 2 enzymes are described in PCT publication WO 93/23050.

More particularly, the present invention relates to a method for treating hyperandrogenic conditions in a human being in need of such treatment by irreversibly inhibiting the human 5α-reductase enzyme without covalently modifying the 5α-reductase enzyme. This method comprises the administration to the human in need of such treatment of a 3-oxo-4-azasteroid having a 1,2-double bond. The 3-oxo-4-azasteroid having a 1,2-double bond is selectively activated by 5α-reductase to produce the covalent adduct with the cofactor NADPH of structural formula (I).

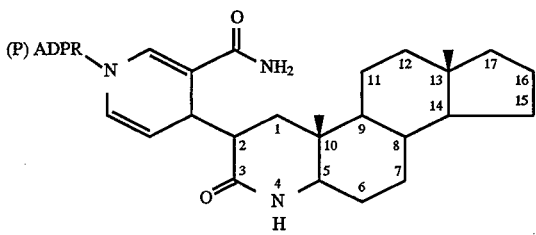

This covalent adduct is released so slowly from the 5α-reductase enzyme that the inhibition of the enzyme is effectively irreversible.

The method of the present invention provides for an inhibitor which displays the characteristics of a suicide inhibitor without covalently modifying the enzyme. Generally, "suicide inhibitors" are inhibitors that deactivate the enzyme by covalent modification of the enzyme protein. Such "suicide inhibitors" are not favored as pharmaceutical agents because the covalently-modified enzyme may be recognized by the immune system of the treated organism as foreign matter and trigger an undesirable immunological response. The non-protein bound adduct of the present invention eliminates the possibility of such an undesirable immunological response.

The long-lived enzyme-bound 3-oxo-4-azasteroid-NADP adduct of the present invention provides further advantages in clinical settings. The method of the present invention provides for sustained inhibition of 5α-reductase even when the dose regimen is interrupted and the levels of the 3-oxo-4-azasteroid drug having a 1,2-double bond drop, as when the patient misses a dose. In this situation of interrupted dosing, 5α-reductase that had been inhibited cannot recover from the inhibition and additional drug is required to inhibit only the 5α-reductase that has been newly synthesized by the patient.

Hyperandrogenic conditions treatable by the method of the present invention include benign prostatic hyperplasia, androgenic alopecia, acne vulgaris, seborrhea, female hirsutism and prostatic carcinoma.

The 3-oxo-4-azasteroids having a 1,2'-double bond useful in the present invention are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices may be administered systemically, by oral administration or by intravenous or intramuscular injection or topically.

For instance, for oral administration in the form of a tablet or capsule, the active drug component can be combined with an oral, non-toxic pharmaceutically acceptable inert carrier such as ethanol, glycerol, water and the like. Capsules containing the product of this invention can be prepared by mixing an active compound of the present invention with lactose and magnesium stearate, calcium stearate, starch, talc, or other carriers, and placing the mixture in gelatin capsule.

Tablets may be prepared by mixing the active ingredient with conventional tableting ingredients such as calcium phosphate, lactose, corn starch or magnesium stearate. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical pharmaceutical compositions may be, e.g., in the form of a solution, cream, ointment, gel, lotion, shampoo or aerosol formulation adapted for application to the skin. Topical pharmaceutical compositions useful in the method of treatment of the present invention may include about 0.001% to 0.1% of the active compound in admixture with a pharmaceutically acceptable carrier.

Topical preparations containing the active drug component can be admixed with a variety of carrier materials well known in the art, such as, e.g., alcohols, aloe vera gel, allantoin, glycerine, vitamin A and E oils, mineral oil, propylene glycol, PPG2 myristyl propionate, and the like, to form, e.g., alcoholic solutions, topical cleansers, cleansing creams, skin gels, skin lotions, and shampoos in cream or gel formulations. See, e.g., EP 0 285 382.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carders to which the compound molecules are coupled. The compounds of the present invention may also be coupled with soluble polymers as targetable drug carders. Such polymers can include polyvinylpyrrolidone, pyran copolymer, polyhydroxypropylmethacrylamidephenol, polyhydroxyethylaspartamide-phenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Advantageously, the active agent of the present invention may be administered in a single daily dose, or the total daily dosage may be administered in dividend doses of two, three or four times daily. The compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the 3-oxo-4-azasteroid having a 1,2-double bond useful in the method of the present invention range from 0.01 to 50 mg per day, and as provided by the advantage of the present invention, doses inadvertently missed will not compromise the therapeutic efficacy. Most preferably, dosages range from 0.1 to 10 mg/day.

The 3-oxo-4-azasteroids of the present invention may be administered on a cyclical regimen. The details of the effective regimen depend on the particular 3-oxo-4-azasteroid administered. For an agent such as finasteride, assuming a $t_{1/2}$ for clearance of 4 hours compared with a $t_{1/2}$ of perhaps two days (10 times as long) for replenishing the enzyme, then the agent would have a 10-fold advantage over a classical drug with the same clearance ability that is not a 3-oxo-4-azasteroid having a 1,2-double bond. The term "classical drug" refers to a pharmaceutically active agent that does not function as an irreversible inhibitor.

The 3-oxo-4-azasteroids having a 1,2-double bond of the present invention may be administered in the form of pharmaceutically acceptable salts. The term "pharmaceutically acceptable salt" is intended to include all acceptable salts such as hydrochloride, hydrobromide, acetate, panoate and the like which can be used as a dosage form for modifying the solubility or hydrolysis characteristics or can be used in sustained release or pro-drug formulations.

Kinetic Model for 3-oxo-4-azasteroid Inhibitors Having a 1,2-double Bond

A kinetic model for mechanism-based inhibition that adequately describes the interaction of finasteride with human 5α-reductase is shown below.

Kinetic Model

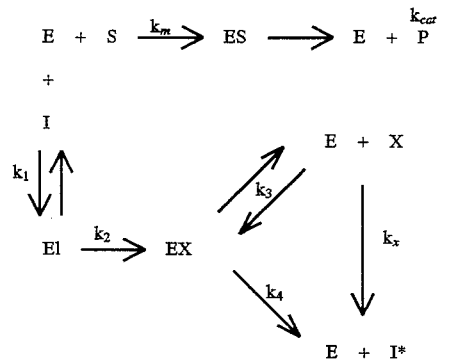

$k_m = 25$ nM  $k_{cat} = 0.075$ s-1  $K_i = (k_2 + k_{-1})/k_1 \geq 100$ nM $k_{on} = k_2/k_i = 3 \times 10^5$ M$^{-1}$ s$^{-1}$  $k_{off} = k_3 + k_4 \leq 3 \times 10^{-7}$ s$^{-1}$ steady-state $K_i^* = k_{off}/k_{on} \leq 1 \times 10^{-2}$ M $k_{on}^x = k_3 = 1 \times 10^6$ M$^{-1}$ s$^{-1}$  $k_{off}^x = k_3 \leq k_{off}$  $k_x = 7 \times 10^{-7}$ s$^{-1}$ -continued
Kinetic Model $K_i^x = (k_{off}/k_{on})^x < 3 \times 10^{-13}$ M The formal kinetic mechanism has been shown to be ordered bi bi, with testosterone adding second and dihydrotestosterone leaving first. The nicotinamide coenzyme has been omitted for clarity. The model proposes that the competitive inhibitor binds rapidly and reversibly to form a weak complex with the enzyme, analogous to the Michaelis complex for a substrate. The enzyme initiates catlysis, and in the process generates a reactive intermediate which forms the high-affinity enzyme-inhibitor complex, EX. This complex eventually turns over to release the transformed inhibitor, I*, or (at least on denaturation) releases the covalent intermediate, X, which slowly decomposes to I* in solution. The formation ($k_2$) and turnover ($k_4$) of the high-affinity enzyme-inhibitor complex appear to be essentially irreversible. In practice, the halflife of the enzyme-inhibitor complex is so long that the inhibition is for all intents irreversible, and release of the inhibitor probably occurs by death of the enzyme rather than turnover to regenerate catalytically competent enzyme.

The model applies in many aspects to both slow-binding, reversible inhibitors and to mechanism-based, irreversible ones. Under the standard assay conditions, the $K_m$ of the baculovirus-expressed enzyme for testosterone was found to be 24.6±0.7 mM at pH 7.2 and 37° C. This $K_m$ value agrees with that determined by Faller, et al. Biochemistry 32:5705–5710 (1993) for the native human prostate enzyme at neutral pH ($K_m$=20±3 nM). The $K_m$ for NADPH was found to be ~1 µM under the assay conditions and 10×$K_m$ testosterone. The turnover number was $k_{cat}$=0.075±0.006 s$^{-1}$ at pH 7.2 and 37° C., as determined by titration with finasteride. From these kinetic constants, $k_{cat}/K_m$= 2.99±0.32×10$^6$M$^{-1}$ s$^{-1}$. Enzyme concentrations calculated from these catalytic constants were used to predict stoichiometries in the experiments below with [$^3$H]finasteride and, in general, were found to give self-consistent results.

Structure-Activity Correlations

The structural features of 3-oxo-4-azasteroids having a 1,2-double bond that confer slow-binding and, by inference, mechanism-based inhibition are addressed in the data of Example 8. Chronologically, these data provided the first indication that 3-oxo-4-azasteroids having a 1,2-double bond might be mechanism-based inhibitors. Three modifications to finasteride were considered: reduction of the $\Delta^{1,2}$ double-bond, methylation of the 3-oxo-4-aza group, and substitution at the 17-position. Second-order rate constants are given for those inhibitors found to be slow-binding, and $k_1$ values for those confirmed to be classical, reversible inhibitors. The conclusions are unambiguous: (1) The 1,2 double-bond is essential to mechanism-based inhibition. (2) Converting the 4-NH— group to 4-N(CH$_3$)— also abolishes the mechanism-based inhibition. And (3) among the mechanism-based inhibitors, large hydrophobic substituents like cyclohexyl- or adamantyl- increase the second-order rate constant $k_{inac}/K_i$ to a level approaching $k_{cat}/K_m$ for turnover of testosterone. Among the nonmechanism-based analogs, these groups cause a parallel decrease in $K_i$ for reversible association, implying that their influence is on binding and not catalysis in the mechanism-based series.

GENERAL METHODS

Labeled [1,2-$^3$H]finasteride had specific activity 23.35 dpm/fmol (10.52 Ci/mmol); [t-butyl-$^{14}$C]finasteride had specific activity 25.66 dpm/pmol (11.56 Ci/mol) and was prepared from ($^{14}$C)-1-butanol. Both radiolabeled compounds were >97% pure by reverse phase high pressure liquid chromatography. The substrate (7-$^3$H)testosterone had specific activity 24.6 Ci/mmol and was purchased from New England Nuclear.

Assay

The standard assay contained 100 pM membrane-bound enzyme suspended in a solution of 25 nM [$^3$H]testosterone (139,000 dpm, carrier free) and 500 µM NADPH in a buffer consisting of 0.1M MOPS, 1 mM EDTA, and 0.1% BSA, at pH 7.20 and 37° C., in a total volume of 100 µL. Ethanol was included at 1% final concentration as the vehicle for introduction of inhibitors. The rate of production of [$^3$H] dihydrotestosterone was approximately constant for up to 2 hours or 10% consumption of substrate. A unit of enzyme activity was defined as 1 pmol product/min, and was equal to 444 fmol enzyme under these conditions.

After quenching the reactions with an equal volume, or more, of water containing 1% trifluoroacetic acid, the [$^3$H] dihydrotestosterone was isolated by direct injection onto a reverse phase C-18 column (Vydac, 4.6×250 mm, 300 Å, 5 micron), which was run in an isocratic system of 40% water (containing 0.1% trifluoroacetic acid) and 60% methanol at 1 ml/min. When tissue extracts were the source of enzyme, the quenched reactions were clarified by centrifugation at 10,000×g before analysis. Retention times were ~13 min for testosterone and ~20 min for dihydrotestosterone. The effluent containing the [$^3$H]dihydrotestosterone peak (6 mL) was collected in a liquid scintillation vial and counted with AQUASOL 2 (14 mL, New England Nuclear) with an efficiency of 0.309. The assay was completely automated using a SUN SPARKSTATION 2 computer interfaced to a ZYMARK robot and ancillary equipment.

Where indicated, measurements were also conducted under conditions that have more traditionally been employed for this enzyme at pH 5.50 and 37° C.

Enzyme Preparation

The native human enzyme was from prostate (type 2) or scalp (type 1) tissue, and the recombinant human enzymes were produced by the baculovirus expression system of Andersson, et al. (Chan, H K, Geissler, W M, Andersson, S, Sex Hormones and Antihormones in Endocrine Dependent Pathology: Basic and Clinical Aspects, M. Motta and M. Serio, eds., Elsevier Science 1994). A comparable baculovirus expression system also has been described recently by Tian et al., Biochemistry, 33:2291–2296 (1994). Enzyme concentrations were determined by titration with finasteride, or [$^3$H]finasteride, or from catalytic activity using kcat and Km values, as described later. The molecular weight was taken to be about 30,000 in estimating enzyme purity.

The enzyme was either used directly as a crude cell homogenate, or isolated as microsomal suspensions by differential centrifugation. In general, the tissue or cell pellet was combined with an equal volume of buffer and dispersed using a high shear force homogenizer (POLYTRON, high speed) for several minutes in an ice bath below 10° C. This procedure was effective in giving uniformly dispersed preparation, and even prolonged homogenization (10 min) did not adversely affect enzyme activity. Saturating levels of cofactor were usually included to improve enzyme stability.

The following results obtained with the recombinant prostate (type 2) isozyme were typical. The baculovirus expression system gave cell pellets containing 1–2 µM enzyme, in which the enzyme constituted ~0.2% of the total protein. There appeared to be contamination with a potent metalloprotease, such that the halflife of the enzyme in the concentrated homogenate was on the order of minutes at 37° C. in the absence of a metal chelator. Consistent with the reported localization of native 5α-reductase in membranes associated with the nuclear envelope, the enzyme sedimented over a wide range of centrifugal force. For instance, disruption of the cell pellet in an equal volume of buffer consisting of 0.1M MOPS, 1M sucrose, 10 mM EDTA, and 100 µM NADPH at pH 7.2, gave a suspension containing 1,436 units of enzyme/mL and 10.5 mg of protein/mL. Fractionation of this suspension gave enzyme distributed as follows: 25% of the activity sedimented at 1,000 g×30 min, 16% sedimented at 10,000 g×30 min, 15% sedimented at 100,000 g×30 min, and 8% remained suspended at 100,000 g×60 min. Some 36% of the activity in the homogenate was unaccounted for after centrifugation. The highest specific activity fractions, those sedimenting between 1,000 and 100,000×g, were enriched less than 2-fold in specific activity. Consequently, the different fractions were used interchangeably, depending on the demands of particular experiments. In these concentrated suspensions, the enzyme was stable indefinitely when frozen at −80° C. and could be repeatedly freeze-thawed with only minor loss of enzyme activity.

Enzyme Sources

The human isozymes were employed exclusively in this research. The native isozymes were from scalp (type 1) or prostate (type 2) tissues, and the recombinant forms were produced by a baculovirus expression system. Except where specified, all data refer to the prostate (type 2) isozyme, the primary target of finasteride. All of the experiments described in this application were also conducted with the recombinant type 1 isozyme, either in parallel or for confirmation. Since the techniques and results were identical, except in the values of the kinetic and inhibition constants, a detailed description is omitted to avoid confusion and repetition. The native and recombinant enzymes appeared to have comparable Km values for testosterone and second-order rate constants for inhibition by finasteride, and were considered interchangeable. The enzyme was employed as crude, membrane-bound preparations, since it has proven to be intractable to purification. By titration with finasteride, as described below, the enzyme constituted ~0.000,1% of the protein in native human prostate tissue preparations, and ~0.1% on average in the baculovirus.

EXAMPLE 1

Rate Constant for Dissociation of Enzyme-Inhibitor Complex

The rate constant for dissociation of the enzyme-inhibitor complex was determined from the rate of release of radioactivity from enzyme-[$^3$H]finasteride complex in the presence of 100-fold excess unlabeled finasteride. The enzyme-[$^3$H]finasteride complex was formed in a solution containing excess enzyme: 21.9 nM enzyme (6 mg protein, ~0.04% pure, taken from the relatively homogeneous 100,000×g supernatant fraction). 9.33 nM [$^3$H]finasteride (0.343 uCi), and 466 µM NADPH in a buffer consisting of 0.1M MOPS, 0.1% BSA, and 10 mM EDTA at pH 7.2 and 37° C. in a total volume of 3.50 mL. The predicted initial halflife for consumption of [$^3$H]finasteride under these conditions is 2 min. and the reaction was presumably complete in one hour (36% inhibition). After 2 hours, exchange was initiated by making the solution 933 nM in unlabeled finasteride (including 1% ethanol). The solution was divided into aliquots (100 µL) which were incubated at 37° C.; each day a sample was removed and frozen away at −80° C. for future determination of bound and free inhibitor.

EXAMPLE 2

Determination of Bound and Free Inhibitor

The concentrations of bound and free radioactivity were determined by ultrafiltration on 10,000 Da cutoff membranes (AMICON, Centricon-10), which were centrifuged several hours at 4° C. Typically, 100 µL samples were diluted to 1 mL with water before ultrafiltration, and portions of the total solution and the filtrate were counted in cocktails containing 1 part aqueous sample to 20 parts Aquasol 2 (efficiency=0.494). The standard error in these determinations was ±5%.

Nonspecific binding was assessed by reversing the order of addition, first blocking the enzyme with excess unlabeled inhibitor before addition of enzyme. These controls indicated 16±2% apparent (nonspecific) binding. Alternatively, heat-denaturation of the enzyme-[$^3$H]finasteride complex above gave a comparable value of 13±2% apparent residual binding, and this was essentially identical to the nonspecific binding of [$^3$H]finasteride observed in the absence of added enzyme: 12±2%. Based on these controls, observed free concentrations were corrected for 16% nonspecific binding by the expression free=free $_{obs}$/(1−0.16). No nonspecific binding (±2%) occurred in denaturation experiments using 7M guanidine hydrochloride. As proof of this method for identifying release of a low molecular weight ligand, solutions of carbonic anhydrase (30,000 Da) and cytochrome c (12,400 Da) in 7M guanidine hydrochloride continued to show >96% retention on these membranes.

EXAMPLE 3

Purification of Dihydrofinasteride

To obtain sufficient transformed inhibitor for mass spectral analysis, a preparation of baculovirus-expressed enzyme was employed that consisted of all protein sedimenting between 1,000 to 100,000×g. The enzyme-[$^3$H]finasteride complex was formed in a solution containing 1.39 µM enzyme (41,000 units, 141 mg protein), 1.14 µM unlabeled finasteride (15.0 nmol), 0.0113 uM tracer [$^3$H]finasteride (1.56 µCi), and 573 µM NADPH, in a buffer composed of 0.1M MOPS, 1M sucrose, and 10 mM EDTA at pH 7.20 in a total volume of 13.1 mL. The enzyme was dispersed in the solution with a dounce and stirred for 45 min as it warmed to room temperature, which produced 73% inhibition. The solution was then dialyzed overnight at 4° C. in 14,000 Da cutoff dialysis tubing (SPECTRAPOR 2) against 2 changes of 4L water containing 1 mM MOPS and 1 mM EDTA at pH 7.20. This resulted in 88% retention of the radioactivity. (Analysis of the radioactivity lost to dialysis indicated 62% chromatographed as [$^3$H]dihydrofinasteride, and the remainder as [$^3$H]finasteride. This corresponds to loss of 8% of the total starting radioactivity as [$^3$H]dihydrofinasteride, implying a partition ratio of 1.08 in this instance.)

The bound radioactivity was released from the enzyme-inhibitor complex by heat denaturation in a boiling water bath for 20 min, and the precipitated protein was removed by centrifugation at 100,000×g for 90 min with recovery of 90% of the bound radioactivity in the supernatant. This solution was further clarified by ultrafiltration through a 10,000 Da cutoff membrane (AMICON, YM-10) with 84% recovery of the radioactivity.

The radioactive species was then purified by reverse phase high pressure liquid chromatography. The solution (21.8 mL) was loaded by multiple injections using a 5 mL sample loop onto the same analytical C-18 column used for the assay (VYDAC, 4.6×250 mm, 300 Å, 5 micron, flow rate=1 mL/min), which had been equilibrated with water containing 0.1% trifluoroacetic acid. Less than 1% oft he applied radioactivity was detected in the effluent during the application and subsequent washing with water for 20 min. The radioactive component was then eluted as a single, sharp peak by a linear gradient from 0–100% methanol over a period of 40 min and appeared at a nominal concentration of 93% methanol. The recovery of the applied radioactivity was only 37%, for reasons that became apparent later, and the overall recovery was 28% of the $^3$H-content in the dialyzed enzyme-inhibitor complex. Mass spectra were recorded on this preparation.

EXAMPLE 4

Identification of Dihydrofinasteride

Enzyme-[$^3$H]finasteride complex (~1 pmol, 25,000 dpm) was denatured in a boiling water bath, combined with 0.5 equivalent of fresh [3H]finasteride, and chromatographed on a reverse-phase column under the same conditions as described for the enzyme assay. This and data from similar chromatograms indicated a single radiolabeled compound was released from the enzyme-inhibitor complex (in ~45% recovery), and was distinct from [3H]finasteride. Comparison to retention times for a mixture of unlabeled finasteride (3 nmol) and authentic dihydrofinasteride (10 nmol), as monitored at $A_{210}$, tentatively identified the unknown as dihydrofinasteride.

EXAMPLE 5

Purification of NADP-dihydrofinasteride Adduct

To prepare the enzyme-inhibitor complex, 22.5 g of a frozen cell pellet from the baculovirus expression system (containing 2 µM recombinant human prostate 5α-reductase) was combined with 22.5 mL 0.1M MOPS buffer at pH 7.20, and the suspension was made 100 µM in NADPH and 2 µM in ($^{14}$C)finasteride (2.84×10$^6$ dpm, a 2-fold excess over the enzyme). This solution was homogenized as described above, and then stirred at room temperature for ~2 hours. After formation of the complex, the excess [$^{14}$C]finasteride was removed by dialysis for 3 days at 4° C. against 2×4,000 mL 0.001M MOPS, 0.001M EDTA, pH 7.2, in SPECTRAPOR-2 dialysis tubing, 14,000 Da cutoff. The recovery, 100.6 mL containing 442 nM enzyme-[$^{14}$C]inhibitor complex, mounted to 40% of the total radiolabel.

After this point, all solutions contained ammonium bicarbonate adjusted to pH 9 with ammonium hydroxide to buffer the free adduct, as employed by Ryerson, et al., Biochemistry, 21:1144–1151 (1982) in preparation of [4-$^3$H] NADH. The dialyzed enzyme-[$^{14}$C]finasteride complex (95.6 mL, 1.085×10$^6$ dpm) was denatured by mixing with 95.6 mL of 95% ethanol containing 2 mL of 1M ammonium bicarbonate, pH 9.0. The suspension was stirred for 30 min at room temperature, then centrifuged at 10,000×g for 45 min to remove most of the insoluble matter. The supernatant contained 93% of the radioactivity.

Preliminary purification was accomplished on a Pharmacia Fast Q-50 anion exchange matrix (5 mL column volume, 150×7 mm) at room temperature. The centrifuged aqueous-ethanol solution (175 mL containing 1.007×106 dpm or 224 nM [$^{14}$C]adduct) was applied to the column (HCO$_{-3}$ form, equilibrated to 0.01M ammonium bicarbonate, pH 9), and the column was developed with 50 mL portions of increasing concentrations of ammonium bicarbonate at pH 9.0, starting at 0.05M and ending at 0.35M in steps of 0.05M. The adduct eluted in the 0.20M and 0.25M ammonium bicarbonate fractions and accounted for 68% of the applied $^{14}$C-label. The flow-through contained 3% of the radiolabel, each of the other fractions contained <0.5%, and the remainder failed to elute. The 0.20M and 0.25M ammonium bicarbonate fractions were pooled and lyophilized in the dark overnight, and the white, fluffy, proteinacious residue was dissolved in 2.0 mL 0.01M ammonium bicarbonate, pH 9. The recovery to this point was 63% of the $^{14}$C-content of the dialyzed enzyme-inhibitor complex.

The solution was centrifuged and applied with rinses to a Pharmacia Mono Q anion exchange column ($HCO_3^-$ form, equilibrated to 0.01M ammonium bicarbonate, pH 9, and 50% methanol). The adduct was eluted with a gradient of 0–0.5M ammonium bicarbonate, pH 9, at a flow rate of 1 mL/min over a period of 50 min. The methanol content was held constant at 50%. The adduct eluted as a single, sharp peak at a nominal concentration of 0.266M bicarbonate and accounted for 98% of the applied radioactivity. The peak $^{14}$C-fractions were pooled, the methanol blown off with argon, and then the solution was lyophilized in the dark to give a clear glass. The purified adduct (672,000 dpm) was dissolved in 400 µL 0.1M ammonium bicarbonate, pH 9, to give a 65.4 µM solution and an overall recovery of 62% from the dialyzed enzyme-inhibitor complex. Spectra were recorded on this solution.

The adduct appears more stable to oxidation, and certainly to dissociation, than its NAD-pyruvate counterpart. The integrity of the NADP-[$^{14}$C]dihydrofinasteride adduct, defined as its ability to form [$^{14}$C]-dihydrofinasteride, was measured by high pressure liquid chromatography on a reverse phase column (VYDAC, 4.6×250 mm, 300 Å, 5 micron, flow rate=1 mL/min) in 60% aqueous methanol. The retention time was about 14 minutes, and was consistently 1.4 min longer than that for [$^3$H]finasteride, as determined by co-injection. The reaction was found to be acid catalyzed. The halflife for decomposition was ~1 min in 0.1M ammonium formate buffer at pH 4.00 and 100° C., and these conditions gave 88% conversion to [$^{14}$C]-dihydrofinasteride at infinite time. Analyzed in this way, the adduct appeared stable for months when stored in (or lyophilized from) ammonium bicarbonate buffer at pH 9 and −75° C. As a positive control, oxidation with 0.001M phenazine methosulfate at neutrality and room temperature for an hour completely abolished the ability to dissociate to [$^{14}$C]-dihydrofinasteride.

Indicative of its amphipathic structure, the adduct displays anomalous behavior on several chromatographic matrices. On reverse phase chromatography in 60% aqueous-methanol under acidic conditions, only [$^{14}$C]-dihydrofinasteride elutes; under neutral conditions, the adduct elutes in the breakthrough volume, followed by [$^{14}$C]-dihydrofinasteride at the normal time. Also, none of the adduct would elute from the Mono Q column at any bicarbonate concentration in the absence of 50% methanol.

All lines of evidence point to the covalent adduct of inhibitor and cofactor. (1) The absorbance and fluorescence spectra resemble those of NAD(P)H, the NAD-pyruvate complex and analogs and the NAD-cyanide addition complex described by Kaplan, et al. (2) On heating, the compound decomposes to ($^{14}$C)dihydrofinasteride with a rate constant of ~6×10$^{-4}$ s$^{-1}$ and halflife of 20 min in water at neutral pH and 100° C., explaining the recovery of dihydrofinasteride in the heat-denaturation experiments above. (3) The decomposition to [$^{14}$C]dihydrofinasteride was abolished by treatment with pyrazine methosulfate, a selective oxidant of the dihydropyridine ring. (4) Securing the identification, the most prominent parent ion peak in its mass spectrum had the correct charge/mass ratio of 1116 Da.

Mass Spectrometry

Mass spectra of the [$^3$H]dihydrofinasteride purified from heat-denatured enzyme-[$^3$H]finasteride complex were recorded by LC/MS/MS on a SCIEX API III mass spectrometer, using a heated nebulizer interface and positive ion detection. Samples were run by direct injection in a mobile phase of 50% aqueous acetonitrile containing 5 mM ammonium acetate and 0.05% trifluoroacetic acid. Only one prominent molecular ion (M+1) at 375 Da was detected in scans up to 2,000 Da, and this gave a daughter ion spectrum identical to that of authentic dihydrofinasteride, as shown in FIG. 7, below. Quantitative analysis with dihydrofinasteride as standard showed that the daughter ion peak intensities were the same as, or more intense (180%) than, predicted from the specific radioactivity of the starting [$^3$H]finasteride, indicating that [$^3$H]dihydrofinasteride was the only significant component in the unknown sample.

The absorbance and fluorescence spectra of the adduct were compared to NADPH. The adduct was absorbance maxima at 260 nm and 325 nm with extenction coefficients of 3.13×104 and 5.88×103M-1 cm-1, respectively, based on 14C-content, and a fluorescence emission maximum at 441 nm. Spectra were obtained in 0.1M ammonium bicarbonate at pH 9, and fluorescence excitation was at the respective long wavelength absorbance maxima. The unusually high extinction coefficient at 260 nm may be caused by residual impurities in the preparation.

The putative [3H]finasteride released from heat-denatured enzyme-inhibitor complex was purified in 28% total recovery. Analysis by mass spectrometry indicated a single prominent molecular ion at (M+1)=375, consistent with dihydrofinasteride.

Identical daughter ion fragmentation patterns were found for this molecular ion and for that of authentic dihydrofinasteride securing the assignment.

Calculations

Data were fit to the appropriate models and velocity equations by nonlinear regression, using a least-squares Marquardt algorithm in a FORTRAN 77 computer program.

The data for slow-binding inhibition were analyzed as reviewed by Morrison et al., Adv. Enzymol. 61:201–301 (1988). The kinetic model is shown in the Description of the Invention. The time courses were fit to an integrated first-order rate equation (Equation 1), where A is product concentration, $v_o$ is the initial velocity, $v_s$ is the infinite-time velocity, and $k_{obs}$ is the first-order rate constant for progression of the enzyme between the two equilibrium states. The velocities at infinite-time were essentially zero.

$$A=v_s t+(v_o-v_s)(1-e^{-k_{obs}t})/k_{obs}+A_o \qquad \text{Equation 1}$$

Since finasteride previously has been shown to be competitive with testosterone using fixed-time assays, this aspect was not addressed and testosterone concentration (S) was simply held constant at $K_m$. The steady-state dissociation constant of the weak, reversible enzyme-inhibitor complex, $K_i$, was obtained by nonlinear regression of calculated initial velocities, $v_o$, to Equation 2. The relationship is identical to that expected for a classical competitive inhibitor.

$$v_o=k_{cat}(E)(S)/(K_m(1+(1/K_i))+S) \qquad \text{Equation 2}$$

The rate constant for conversion of the weak complex to the high-affinity one, $k_2$, was obtained by nonlinear regression to Equation 3, which also is a function of $K_i$. The equation applies strictly to reversible, non-mechanism-based inhibitors that are not turned over, but is an excellent approximation for finasteride. Since the formation of the high-affinity complex appears to be irreversible, based on the absence of detectable exchange of [$^3$H]finasteride out of the enzyme-inhibitor complex, the reverse rate constant, $k_{-2}$, was taken to be zero.

$$k_{obs} = k_{-2} + k_2[(I/K_i)/(1+(S/K_m)+(I/K_i))]$$  Equation 3

For inhibition of the prostate (type 2) isozyme by finasteride, these fits were relatively insensitive to the denominator term $I/K_i$, indicating that $K_i$ for this complex was greater than the accessible range of inhibitor concentrations. Consequently, only the second-order rate constant, $k_2/K_i$, is known with certainty. This is not the case for the skin (type 1) isozyme, where this complex was kinetically significant and had $K_i$=360 nM, Tian et al., supra.

Noncovalent binding

The high-affinity complex does not appear to involve a covalent bond between finasteride and the enzyme. Evidence for this comes from several methods of denaturation of the enzyme-[$^3$H]finasteride complex, using ultrafiltration on 10,000 Da membranes to define bound and free. Among these, heat denaturation in a boiling water bath for 2 minutes released >96% of the radiolabel, suspension in 45% aqueous ethanol solution released >77%, and solution in 7M guanidine hydrochloride released >99%.

Identification of dihydrofinasteride

The radioactive species released spontaneously from the enzyme-[$^3$H]finasteride complex was tentatively identified as the reduction product, [$^3$H]-1,2-dihydrofinasteride, by co-chromatography on a reverse phase column. This radiochromatogram was observed when [$^3$H]finasteride (1 equivalent), as reference standard, was co-injected with a solution of heat-denatured [$^3$H]finasteride-enzyme complex (2 equivalents). As shown in the offset, the unknown peak was tentatively identified as 1,2-dihydrofinasteride by comparison to retention times of authentic unlabeled compounds.

EXAMPLE 6

Rate Constant for Formation of Enzyme-Inhibitor Complex with Finasteride

The potency of finasteride is evident in the nearly complete suppression of the activity at infinite time that was seen at even the lowest practical concentrations of finasteride (2 nM). This implies that the overall equilibrium constant, $K_i^*$, is <100 pM. For the native enzyme the time courses for slow-binding inhibition correspond to a second-order rate constant for formation of the high-affinity complex from free enzyme and inhibitor of $k_{on} = k_2/K_i = 2.53 \pm 0.03 \times 10^5 M^{-1} s^{-1}$, as measured under the traditional assay conditions at pH 5.5 and 37° C. Essentially the same rate constant was obtained using the recombinant enzyme, $k_{on} = 3 \times 10^5 M^{-1} s^{-1}$, under the standard assay conditions of pH 7.2 and 37° C.

The initial velocities of the theoretical lines were independent of finasteride concentration, indicating that a significant mole fraction of the enzyme was not present as the preliminary complex over this concentration range. Similarly, the first-order rate constants describing the time courses were nearly linearly dependent on inhibitor concentration, as predicted in the absence of a kinetically significant preliminary complex. The theoretical line corresponds to $K_i$=100 nM for the preliminary complex, which is well above the accessible inhibitor concentration range. Assuming this minimum value for $K_i$, conversion of the proposed reversible, loose complex to the high-affinity one takes place with a rate constant $k_2 \geq 0.025$ s$^{-1}$ and halflife of <30 seconds.

These conclusions and kinetic constants agree with the recent work of Faller, et al. (10), who concluded that $k_{on}=2.7 \times 10^5$ M$^{-1}$ s$^{-1}$ and that the dissociation constant $K_i$ is greater than 150 nM at pH 7.0 for inhibition of the native human prostate enzyme by finasteride.

EXAMPLE 7

Determination of Rate Constant for Dissociation of Enzyme-finasteride Complex and Partition Ratio The time courses for development of inhibition argued it would be foolish to look for recovery of enzyme activity upon dissociation of the enzyme-inhibitor complex, as might be driven by dilution, dialysis, or competition with testosterone. Assuming $K_i^* < 100$ pM, the rate constant for association predicts the halflife for dissociation (or turnover) of the enzyme-inhibitor complex is >6 hours at 37° C. This is longer than the halflife of the free enzyme in these crude membrane preparations, which was 4.66±0.41 hours at 37° C. in the absence of cofactor. Consequently, active enzyme would not be expected to accumulate during dissociation, and in a practical sense inhibition by finasteride has the appearance of being irreversible.

The stability of the enzyme-inhibitor complex was determined from the rate of release of [$^3$H]inhibitor from preformed enzyme-[$^3$H]finasteride complex, measured in the presence of unlabeled finasteride to drive the anticipated exchange. The exchange solution contained 9.33 nM preformed, membrane-bound enzyme-[$^3$H]finasteride complex and a 100-fold excess of unlabeled finasteride, and the dissociation was monitored at pH 7.2 and 37° C. As described in the General Methods Section, concentrations of bound and free radiolabel were determined by ultrafiltration through 10,000 Da cutoff membranes. The time course for appearance of free [$^3$H]inhibitor was determined over a period of 3 weeks. These data indicate first-order decay of the enzyme-inhibitor complex with a rate constant $k_{off}$ = 2.57±0.03×10$^{-7}$ s$^{-1}$, equivalent to a halflife of 31.2±0.4 days. Given the crude, membrane-bound state of the enzyme, slow degradation of the enzyme and membrane may well contribute some, or all, to the observed rate of release, and the true rate constant for dissociation of the enzyme-inhibitor complex may be even smaller than this value.

Partition Ratio

A characteristic of mechanism-based inhibitors is that, once activated by an enzyme, they may partition between two fates: harmless dissociation away to free solution, and lethal inactivation of the enzyme. As developed by Walsh (13), the ratio of the rate constant for overall consumption to the rate constant for inactivation, the partition ratio, provides an important measure of the efficiency of such inhibitors: the lower the partition ratio, the fewer molecules of a drug that are required to inhibit the target enzyme. The partition ratio for finasteride appears to be <=1.07. Evidence for this comes from the off-rate experiment (above) and from preparation of the enzyme-inhibitor complex described in the General Methods section. Finasteride is an unusually efficient mechanism-based inhibitor by this criterion.

In the case of the free [$^3$H]-inhibitor that had accumulated over one month during determination of the rate constant for dissociation, no [$^3$H]H$_2$O was observed and the recovery of [$^3$H]-1,2-dihydrofinasteride accounted for >95% of the free tritium released from the [$^3$H]finasteride-enzyme complex. That no untransformed [$^3$H]finasteride was detected, despite the potential for back-exchange with the unlabeled finasteride pool, implies formation of the high-affinity enzyme-inhibitor complex is essentially irreversible.

Assignment of the transformed inhibitor as 1,2-[$^3$H] dihydrofinasteride was confined by mass spectroscopy. The purification is described in detail in the General Methods Section. Employing heat-denaturation to release the inhibitor from the membrane-bound enzyme-[$^3$H]finasteride complex, the radioactive component was purified by centrifugation (90% recovery), ultrafiltration (84% recovery), and reverse phase high pressure liquid chromatography (37% recovery). The purified radioactive component gave a dominant molecular ion at 375 Da, consistent with dihydrofinasteride. Comparison of its daughter ion spectrum to that of authentic dihydrofinasteride provided incontrovertible evidence for the assignment.

Covalent intermediate

Eventually, it became evident that dihydrofinasteride is not the immediate product released upon denaturation of the enzyme-inhibitor complex. Several lines of evidence pointed to release of a much more polar [$^3$H]-labeled component. Among these, it was disconcerting that recoveries of [$^3$H]dihydrofinasteride on the reverse phase column were often only 35–45% of the radioactivity released from heat-denatured enzyme-inhibitor complex, the remainder never eluting (under acidic conditions). Moreover, it was found that <5% of the radioactivity released by denaturation in guanidine hydrochloride would partition into chloroform, a polarity completely inconsistent with [$^3$H] dihydrofinasteride. It is now clear that this polar intermediate accounts for most, or all, of the radioactivity released by any denaturation method, chromatographs anomalously, and is inadvertently converted to [$^3$H]dihydrofinasteride during heat-denaturation.

Decomposition of NADP-dihydrofinasteride adduct

The rate constant for nonenzymatic breakdown of the covalent intermediate to NADP$^+$ and dihydrofinasteride was determined under the same conditions used for the enzyme kinetic constants. See Example 5. A constant $k_x = 7.21 + 0.27 \times 10^{-7}$ s$^{-1}$ and a halflife of 11.1±0.4 days at pH 7.2 and 37° C. was calculated. The formation of [$^{14}$C]dihydrofinasteride went to 75% completion at infinite lime, presumably due to competing side reactions like oxidation of the dihydropyridine ring. In contrast, the NAD-pyruvate adduct is so unstable as to preclude normal kinetic measurements.

EXAMPLE 8

Inhibition of 5α-reductase by NADP-dihydrofinasteride Adduct

The rate constant for binding of the free NADP-dihydrofinasteride complex to the enzyme was determined from time courses comparable to those described for slow-binding inhibition by finasteride. For this 3-oxo-4-azasteroid inhibitor having a 1,2-double bond, the binding was competitive with the first substrate (NADPH) and independent of saturating concentrations of the second (testosterone). This pattern was consistent with binding of the inhibitor to both E-NADP$^+$ and free E forms of the enzyme, and agrees with the pattern expected for a collected-product inhibitor. By extrapolation to zero pyridine-nucleotide cofactor concentration, as $k = k_{obs} *(1+(\text{NADPH})/K_m)$, the rate constant for binding of the adduct to free enzyme is $k_{-3} = \sim 1 \times 10^6$ M$^{-1}$ s$^{-1}$. This is slightly faster than finasteride forms the high-affinity complex in the forward direction, and approaches the second-order rate constant $k_{cat}/K_m$ for overall turnover of testosterone by this enzyme.

In the forward direction, the rate constant for release of the adduct (either intact or perhaps as free dihydrofinasteride) from competent enzyme has to be less than or equal to the rate constant observed for decay of the enzyme-[$^3$H]finasteride complex to [$^3$H]dihydrofinasteride of 3×10$^{-7}$ s$^{-1}$. Consequently, from the ratio of these rate constants, the dissociation constant of the NADP-dihydrofinasteride complex from the enzyme, is $K_i^* < 3 \times 10^{-13}$ M.

The decay of the isolated complex to NADP+ and [$^{14}$C] dihydrofinasteride was measured as a function of time to determine the rate constant for nonenzymatic decomposition of NADP-dihydrofinasteride. The complex (235 nM) was incubated in 0.1M MOPS, 0.1% BSA, and 1 mM EDTA at pH 7.2 and 37° C., and fractions were taken each day and stored at –75° C. These were later analyzed by reverse phase chromatography as described for the assay using a neutral isocratic system of 60% methanol, where [$^{14}$C] dihydrofinasteride has a retention time of 14 min. The y-axis is expressed relative to the total $^{14}$C-label in each sample injected (2,410 dpm). The reaction went to 0.753 completion at infinite time, as determined by heating at 100° C. The results, as determined by nonlinear regression are consistent with first-order decay with a rate constant $k_x = 7.21 + 0.27 \times 10^{-7}$ s$^{-1}$ and 0.754±0.015 conversion at infinite time as determined by nonlinear regression.

EXAMPLE 9

Structural Requirements for Formation of NADP-steroid Adducts

Permutations of three structural changes to finasteride were tested for their ability to abolish time-dependent inhibition. All compounds were tested at their apparent IC$_{50}$ values at pH 5.5 and 37° C. Those displaying slow-binding inhibition are identified by $k_{on}$ values, which were determined as described for finasteride above. Those for which no time-dependent inhibition was found are identified by apparent K$_i$ values. The data indicate that 1,2-unsaturation and free -4-NH— moieties are essential for slow-binding and, by inference, for high-affinity inhibition through formation of analogous NADP-steroid complexes.

TABLE 1

Structural requirements for formation of NADP-steroid adducts

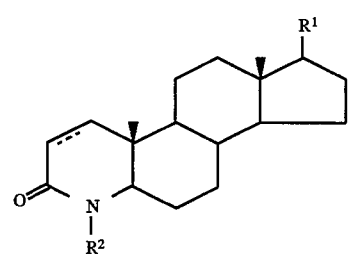

| Compound # | R$^1$ | R$^2$ | 1,2 double bond? | $k_{on}$ 10$^5$ × M$^{-1}$s$^{-1}$ | K$_i$ nM |
|---|---|---|---|---|---|
| 1 | —CONH-t-butyl | H | yes | 2.53 | — |
| 2 | —CONH-t-butyl | H | no | — | 8.0 |
| 3 | —COOCH$_3$ | H | yes | 0.85 | — |
| 4 | —COOCH$_3$ | CH$_3$ | yes | — | 960.0 |
| 5 | —CO-cyclohexyl | H | yes | 28.00 | — |
| 6 | —CO-cyclohexyl | H | no | — | 0.3 |
| 7 | —CO-cyclohexyl | CH$_3$ | yes | — | 13.0 |
| 8 | —CO-cyclohexyl | CH$_3$ | no | — | 0.2 |
| 9 | —CONH-2-adamantyl | H | yes | 47.00 | — |
| 10 | —CONH-2-adamantyl | CH$_3$ | no | — | 0.5 |

These results demonstrate that the unsaturation in the A ring is necessary, but not sufficient, for the time dependent inhibition by 3-oxo-4-azasteroids. This mechanism of inhibition requires both the unsaturation in the A ring and the NH-azasteroid.

EXAMPLE 10

Inhibition of the Human Skin Isozyme

Parallel research with the recombinant human skin (type 1) isozyme indicates finasteride and other 3-oxo-4-aza steroids having a 1,2 double-bond have the same mechanism of inhibition against this enzyme, but finasteride, in particular, binds with a much smaller second-order rate constant, kon=~3×10³ M⁻¹ s⁻¹. This rate constant is ~1% that against the prostate (type 2) isozyme, making finasteride selective for the prostate form. Formation of the adduct appears to be less efficient, taking place with a partition ratio of ~2. The same covalent NADPH-[³H]dihydrofinasteride adduct was released on denaturation of the enzyme-[³H]finasteride complex. The rate constant for spontaneous release of [³H] inhibitor (composition not determined) from membrane-bound preparations of this complex is koff=~6×10⁻⁷ s⁻¹ at 37° C., which corresponds to a halflife of 2 weeks for the enzyme-inhibitor complex. The ratio of these rate constants predicts a steady-state $K_i^*$ of <200 pM.

EXAMPLE 11

Comparison of Activity of Inhibitors Between Type 1 and Type 2 Human Enzyme

Following the procedures of Example 9, the compounds below were each tested with both human type 1 and type 2 enzyme. The results are shown below.

TABLE 2

Activity against human type 1 inhibitor

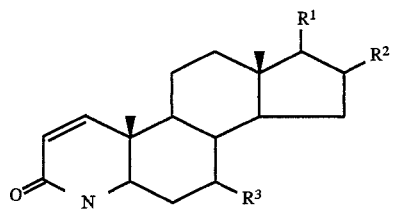

| Compound # | R¹ | R² | R³ | IC$_{50}$ nM | k$_{on}$ M⁻¹s⁻¹ |
|---|---|---|---|---|---|
| 11 | H | —O—(p-chlorophenyl) | CH₃ | 8 | 1.7 × 10⁵ |
| 12 | —(CH₂)₂CONH-4-pyridyl | H | H | 2.8 | 1.7 × 10⁵ |
| 13 | —CH₂CN | H | H | 3 | 1.8 × 10⁵ |
| 14 | —CH(CH₃)(OCH₃) | H | H | 1.8 | 2.0 × 10⁵ |

TABLE 3

Activity against human type 2 inhibitor

| Compound # | IC$_{50}$ nM | k$_{on}$ M⁻¹s⁻¹ |
|---|---|---|
| 11 | >10,000 | 0.5 × 10² |
| 12 | 3,500 | 1.4 × 10² |
| 13 | 8,400 | 1.4 × 10² |
| 14 | 5,400 | 1.3 × 10² |

Based on the data shown in Tables 2 and 3, the compounds have the following selectivities:

TABLE 4

Selectivities for human 5α-reductase type 1

| Compound # | selectivity |
|---|---|
| 11 | 3,300 |
| 12 | 1,200 |
| 13 | 1,200 |
| 14 | 1,600 |

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A compound which is the covalent adduct formed from a 3-oxo-4-azasteroid having a 1,2-double bond and the cofactor NADPH by the activation of the 3-oxo-4-azasteroid having a 1,2 double bond by a 5α-reductase enzyme, provided that the 3-oxo-4-azasteroid having a 1,2-double bond is not:

finasteride

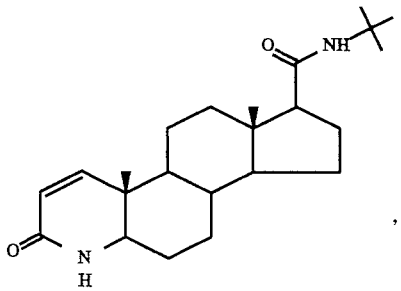

(a)

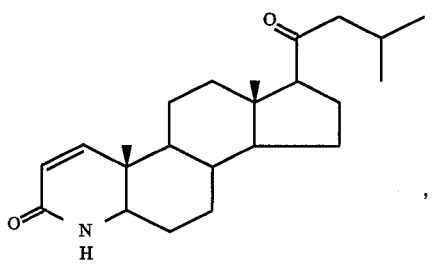

or

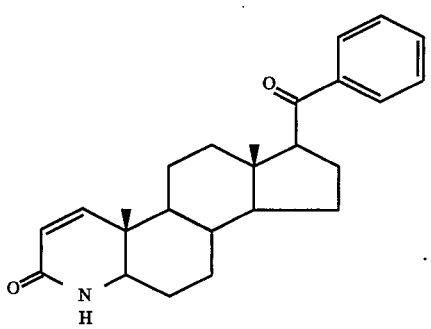

2. The compound of claim 1 provided the 3-oxo-4-azasteroid having a 1,2-double bond is not:

(a) finasteride

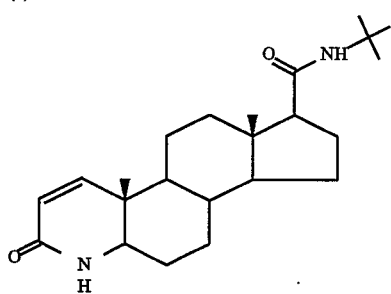

(b)

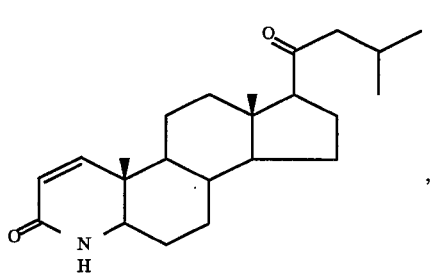

(c)

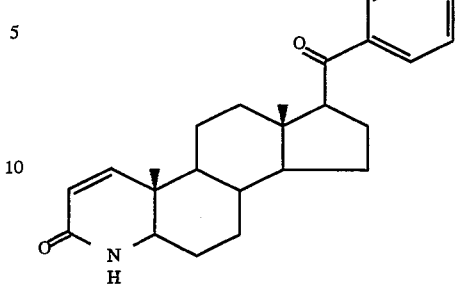

(d)

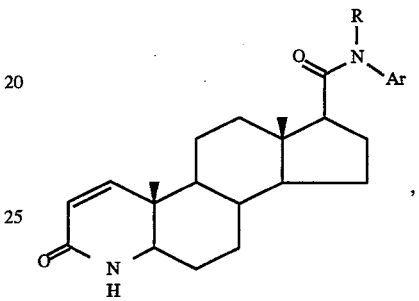

where R = H or lower alkyl,
and Ar = optionally substituted aryl or heteroaryl (e)

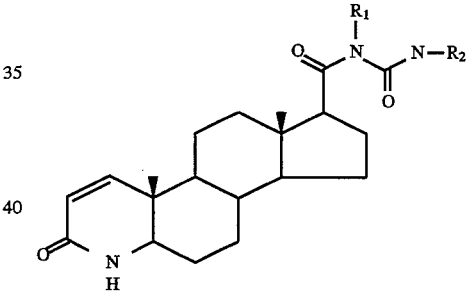

where $R_1$ and $R_2$ are independently selected from H and lower alkyl.

3. The compound of claim 1 of structural formula (I)

(I)

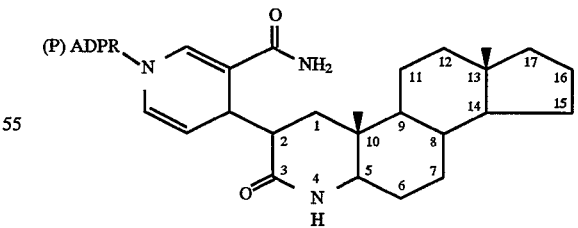

wherein:

the steroid portion of the compound is optionally substituted at one or more of the 17, 16, 15 and 7 positions.

4. A compound of structural formula (I)

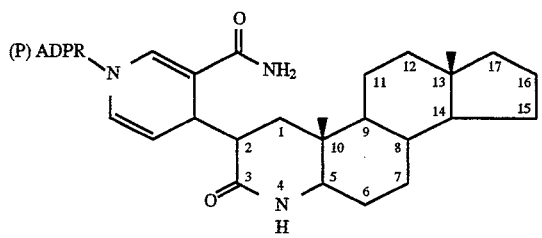

(I)

wherein:
the steroid portion of the compound is optionally substituted at one or more of the 17, 16, 15 and 7 positions, in substantially pure form.

5. The compound of claim 4 of the structural formula below:

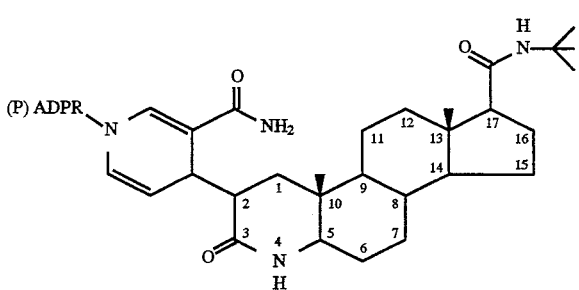

6. A pharmaceutical composition comprising the compound which is the covalent adduct formed from a 3-oxo-4-azasteroid having a 1,2-double bond and the cofactor NADPH by the activation of the 3-oxo-4-azasteroid having a 1,2 double bond by 5α-reductase enzyme.

7. The pharmaceutical composition of claim 6 wherein the covalent adduct is of structural formula (I):

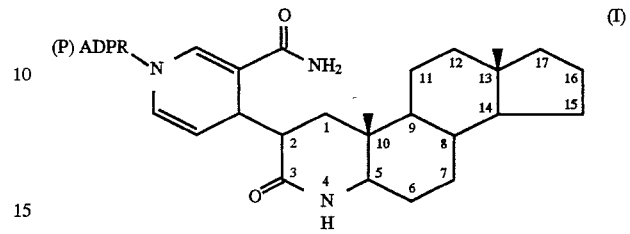

(I)

8. The pharmaceutical composition of claim 6 wherein the covalent adduct is of the structural formula below:

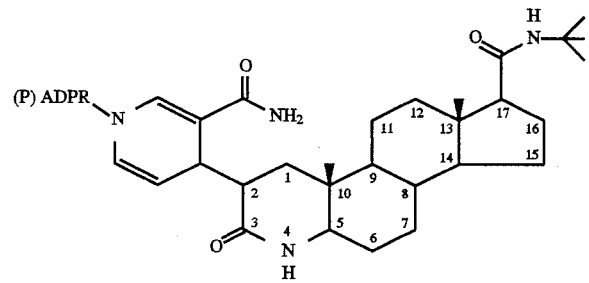

* * * * *